US00PP28864P3

(12) United States Plant Patent
Snijder

(10) Patent No.: US PP28,864 P3
(45) Date of Patent: Jan. 9, 2018

(54) POINSETTIA PLANT NAMED 'EURZ0001'

(50) Latin Name: *Euphorbia pulcherrima*
Varietal Denomination: EURZ0001

(71) Applicant: SYNGENTA PARTICIPATIONS AG, Basel (CH)

(72) Inventor: Ronald Snijder, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 80 days.

(21) Appl. No.: 14/545,661

(22) Filed: Jun. 3, 2015

(65) Prior Publication Data

US 2016/0007518 P1 Jan. 7, 2016

(30) Foreign Application Priority Data

Jul. 2, 2014 (CA) ..... 14-8381
Feb. 2, 2015 (QZ) ..... PBR 2015/0271

(51) Int. Cl.
*A01H 5/02* (2006.01)

(52) U.S. Cl.
USPC ..... Plt./306

(58) Field of Classification Search
USPC ..... Plt./263.1, 302, 303, 306
See application file for complete search history.

(56) References Cited

U.S. PATENT DOCUMENTS

PP14,559 P2 * 2/2004 Drewlow ..... A01H 5/00 Plt./306
PP22,035 P2 * 7/2011 Zerr ..... A01H 5/00 Plt./307

OTHER PUBLICATIONS

Broertjes et al. 1978. Application of Mutation Breeding Methods in the improvement of Vegetatively Propagated Crops. Elsevier Scientific Publishing Company pp. 118-119.*
Pot Plants 2015 Catalog. FloriPro Services; Syngenta. http://www.blondyromania.ro/pdf/BlondyRomania_Catalog_Cyclamen_Poinsettia_Crizanteme_2015.pdf. 8 pages.*

* cited by examiner

*Primary Examiner* — Susan McCormick Ewoldt
*Assistant Examiner* — Karen Redden
(74) *Attorney, Agent, or Firm* — Dale Skalla

(57) ABSTRACT

A new Poinsettia plant named 'EURZ0001' particularly distinguished by its pink flower color, relatively large inflorescences with the bracts a little upright directed, early flowering response, dark green foliage, ovate leaves with only weak lobes, and medium to strong growth habit with good branching.

2 Drawing Sheets

Latin name of the genus and species of the plant claimed: *Euphorbia pulcherrima.*

Varietal denomination: 'EURZ0001'.

BACKGROUND OF THE NEW PLANT

The present invention comprises a new Poinsettia, botanically known as *Euphorbia pulcherrima*, and hereinafter referred to by the variety name 'EURZ0001'.

'EURZ0001' is a product of a planned breeding program. The new cultivar has pink bract color, relatively large inflorescences with the bracts a little upright directed, early flowering response, dark green foliage, ovate leaves with only weak lobes, and medium to strong growth habit with good branching.

'EURZ0001' originates from an induced mutation selected in Enkhuizen, Netherlands in November-December 2011 among flowering greenhouse plants of the parent variety.

The parent was the commercial plant designated 'SYEP22432', also known as 'Titan Red', and patented as U.S. Plant Pat. No. 22,035, with bright red bract color, somewhat larger dark green leaves, upright and vigorous habit, and early flowering response.

Young plants of the parent variety had been exposed to a mixture of X-ray and Gamma irradiation in Enkhuizen, Netherlands. The treated plants were then grown out in a greenhouse Enkhuizen, Netherlands.

During the flowering season in November-December 2011, 'EURZ0001' was discovered and selected as a single mutated plant. The first asexual propagation was made a few months later, by taking shoot tip cuttings from the mutated plant, which were grown out and used for the first flowering trial in Enkhuizen, Netherlands in the fall of 2012. Since then, the plant has been repeatedly asexually reproduced by cuttings in Enkhuizen, Netherlands, and found to be true to type, uniform and stable for the new characteristic.

BRIEF SUMMARY OF INVENTION

Horticultural examination of plants grown from cuttings of the plant initiated in the summer of 2012, and continuing thereafter, has demonstrated that the combination of characteristics as herein disclosed for 'EURZ0001' are firmly fixed and are retained through successive generations of asexual reproduction.

'EURZ0001' has not been observed under all possible environmental conditions. The phenotype may vary significantly with variations in environment such as temperature, light intensity and day length.

Plant Breeder's Rights for this cultivar were applied for in Canada on Jul. 2, 2014, No. 14-8381 and in the European Union (CPVO) on Feb. 2, 2015, No. 2015/0271.

The following traits have been repeatedly observed and are determined to be basic characteristics of the new variety. The combination of these characteristics distinguishes this Poinsettia as a new and distinct variety.

BRIEF DESCRIPTION OF THE PHOTOGRAPHS

Figure 1:
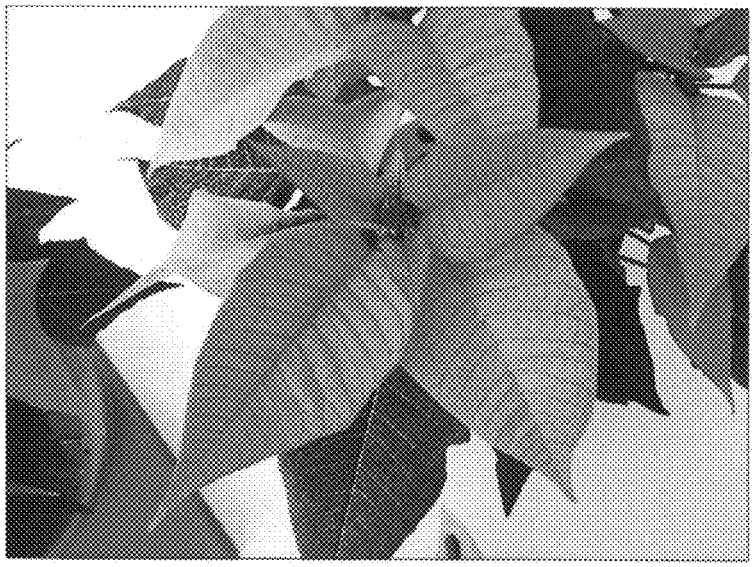

The accompanying photographic drawing shows typical flower and foliage characteristics of 'EURZ0001' with colors being as true as possible with an illustration of this type. The photographic drawings show flowering potted plants of the new variety. FIG. 1, shows a close view of the flower bracts, FIG. 2, a view from above on a young flowering plant, and in FIG. 3, a view of a whole plant in full flower.

DETAILED BOTANICAL DESCRIPTION

The measurements were taken in Hauwert, Netherlands in mid-December 2014 on about 20 week old plants growing in a greenhouse. Culture of these plants had started in late July 2014 with planting of rooted cuttings into 12 cm pots and terminal pinching about 2 weeks later. The plants were grown under natural day light in the fall (no black cloth to initiate earlier flowering) and at the moderately warm temperature of 18° C. for the bench heating.

Figure 2:
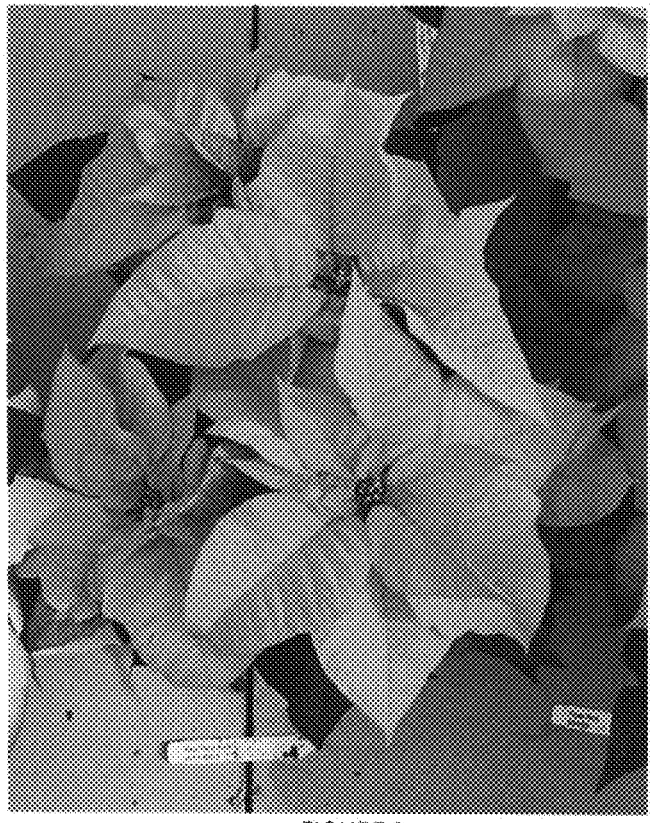
Figure 3:
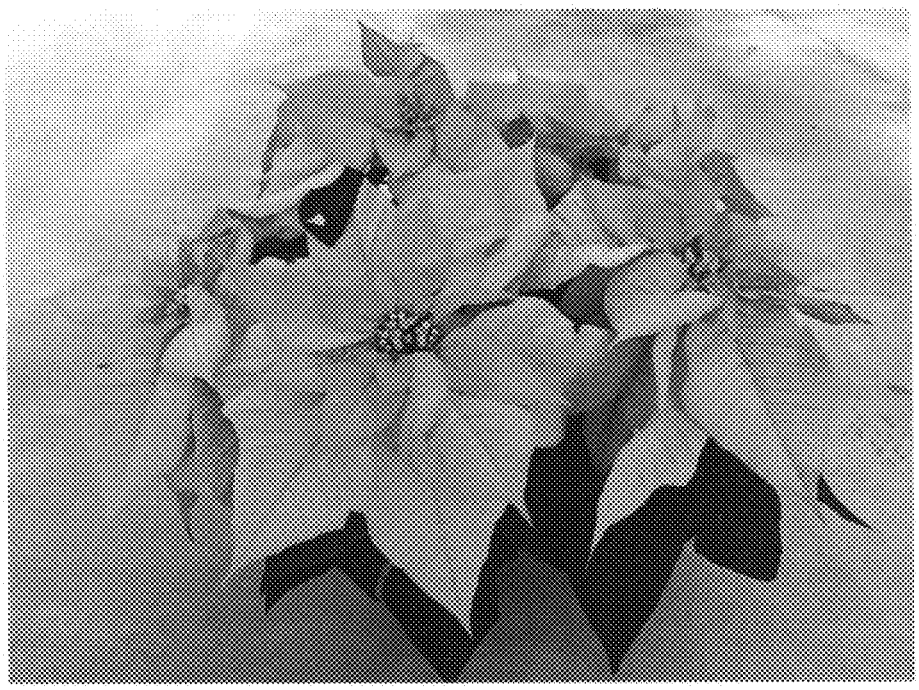

The aforementioned photographs: FIG. 1 was taken in Hauwert, Netherlands in mid-December 2014. The plants were from the greenhouse trial described above. FIG. 2 was taken in Monroeville, N.J. on Nov. 20, 2013 at the start of the natural flowering season, and FIG. 3 shows a plant in full flower from an exhibition ('Pack trials') taken on Apr. 15, 2015 in Gilroy, Calif.

Color references are made to The Royal Horticultural Society Colour Chart (R.H.S.) 2001.

TABLE 1

DIFFERENCES BETWEEN THE NEW VARIETY 'EURZ0001' AND A SIMILAR VARIETY

| | 'EURZ0001' | 'FISMIRPINK' (Commercially 'Mira Pink', not patented) | EURZ0002 |
|---|---|---|---|
| Bract color: | 51 A-C | 53D | 2 D |
| Leaf blade length: | 5 cm | 4-4.5 cm | 6.5 cm |
| Bract shape | Ovate, with shallow lobes | Ovate to almost deltoid, with deep lobes | Ovate, with very shallow lobes |
| Internodes: | Longer | Shorter | |
| Plant habit: | more open | More compact | more open |
| Cyathia, maturity: | Later | Earlier | |
| Plant habit | More upright | Wider, branches more horizontally directed | |

Plant:

*Form, growth and habit.*—Shrub, with the branches slanting upright, good branching.

*Plant height (inflorescence included).*—About 20 cm.

*Plant width.*—About 40 cm.

Roots:

*Number of days to initiate roots.*—18-20 days at about 24 degrees C.

*Number of days to produce a rooted cutting.*—24-26 days at 24 degrees C.

*Type.*—Fine, fibrous, free branching.

*Color.*—RHS N155B but whiter.

Foliage:

*Arrangement.*—Alternate, 6-9 leaves per branch.

*Immature, leaf color, upper surface.*—Approximately RHS 143A.

*Immature, leaf color, lower surface.*—RHS 144A.

*Mature, leaf color, upper surface.*—RHS 139A.

*Mature, leaf color, lower surface.*—RHS 137B.

*Length.*—5 cm.

*Width.*—7-10 cm.

*Shape.*—Ovate, with 2 to 4 shallow lobes.

*Base shape.*—Rounded.

*Apex shape.*—Acuminate, a little twisted sometimes.

*Margin.*—Entire; lobes, if present, are usually rounded.

*Aspect.*—Leaf blades are downwards directed.

*Texture, upper surface.*—Smooth.

*Texture, lower surface.*—Smooth, apart from the protruding veins.

*Color of veins, upper surface.*—RHS 144B at the base.

*Color of veins, lower surface.*—RHS 144C.

*Petiole color, upper surface.*—RHS 177B.

*Petiole color, lower surface.*—RHS 152D.

*Length.*—Most often 5-6 cm.

*Diameter.*—0.2 cm.

*Aspect.*—Horizontally to upward directed.

*Texture.*—Glabrous.

Stem:

*Quantity of main branches per plant.*—About 4.5.

*Color of stem.*—Mainly RHS 144A; RHS 175D at the top section (topmost 2-3 cm of the length).

*Length of stem.*—13-15 cm.

*Diameter.*—0.7 cm.

*Length of internodes.*—3 cm.

*Texture.*—Glabrous.

*Color of peduncle.*—RHS 144B to RHS 144C.

*Length of peduncle.*—0.2-0.3 cm.

*Peduncle diameter.*—0.2 cm.

*Texture.*—Glabrous.

Inflorescence:

*Type.*—Terminal cyme with surrounding whorl of colored bracts.

*Flowering, botanically (opening of the stamen, shedding of pollen).*—Around December 1.

*Flowering, commercially (sufficiently colored bracts).*—In about mid-November.

*Flowering response time.*—About 6.5 weeks from equinox.

*Duration of flowering.*—Depends much on light and environment; a minimum of 4-6 weeks of 'shelf' life.

*Fragrance.*—Absent.

*Shape of inflorescence.*—Rosette-like whorl, star-shaped, not quite closed in the center; bracts horizontally to upward directed.

*Diameter of inflorescence.*—25-27 cm.

*Inflorescence, vertical diameter.*—5-10 cm.

*Number of completely colored bracts per inflorescence (sized over 2 cm).*—12-14.

*Single bract, shape.*—Ovate with relatively long, pointed tips, without or with very weak lobes.

*Bract, apex.*—Acuminate.

*Bract, base.*—rounded.

*Single bract, length of blade.*—11.5-12 cm, younger bracts diminishing in size.
*Single bract, width of blade.*—8.8 cm.
*Bract color, upper side.*—Ranges from RHS 51A for young bracts to RHS 51C for the older and larger bracts.
*Bract color, lower side.*—Near RHS 51D.
*Vein color, upper surface.*—RHS 47B.
*Vein color, lower surface.*—Approximately RHS 48A.
*Texture.*—Weakly rugose, glabrous.
*Bract petiole color, upper surface.*—RHS 185A.
*Bract petiole color, lower surface.*—RHS 183D.
*Bract petiole, length.*—About 2.0-3.0 cm, shorter with younger bracts.
*Bract petiole diameter.*—0.2-0.3 cm.

Cyme (true inflorescence):
*Cyme, diameter.*—1.5 cm.
*Number of cyathia.*—8-9, borne in a tight cluster.
*Cyathium, shape.*—Ovate.
*Cyathium, diameter.*—0.4-0.5 cm.
*Cyathium, length.*—0.6 cm.
*Color.*—RHS N144A and N144B, with RHS N144B mostly at the base.
*Nectar cups.*—Usually one per cyathium.
*Nectur cup, width.*—0.3 cm.
*Nectar cup, color.*—RHS 30D, very light.

Reproductive organs:
*Stamen* (*actually reduced male florets*).—Usually in a small bunch of 10-20 at the top of the cyathium.
*Shape.*—Strap-like.
*Filament length.*—0.4-0.5 cm.
*Filament color.*—RHS 45B.
*Anther color.*—RHS 11A.
*Anther diameter.*—0.1 cm.
*Pollen quantity.*—Moderate (normal quantity).
*Pollen color.*—RHS 12A.
*Female flowers.*—Not observed in this trial; appear (if at all) in mid-winter, as occurrence depends much on light intensity; appear about 4 weeks later than the stamen: a single female flower emerges from the top of the cyathium with a short pedicel.
*Fertility/seed set.*—Has not been observed on this plant.

Disease/pest resistance: Disease/pest resistance has not been observed on this plant.

What is claimed is:

1. A new and distinct variety of Poinsettia plant named 'EURZ0001', substantially as illustrated and described herein.

* * * * *